US012778508B2

(12) United States Patent
Saeki

(10) Patent No.: US 12,778,508 B2
(45) Date of Patent: Nov. 3, 2026

(54) ASSIST TOOL AND SENSOR KIT

(71) Applicant: NIHON KOHDEN CORPORATION, Tokyo (JP)

(72) Inventor: Kota Saeki, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 18/933,549

(22) Filed: Oct. 31, 2024

(65) Prior Publication Data

US 2025/0152100 A1 May 15, 2025

(30) Foreign Application Priority Data

Nov. 9, 2023 (JP) ................................ 2023-191460

(51) Int. Cl.
*A61B 5/00* (2006.01)
*A61B 5/024* (2006.01)
*A61B 5/1455* (2006.01)

(52) U.S. Cl.
CPC ........ *A61B 5/6826* (2013.01); *A61B 5/02438* (2013.01); *A61B 5/14552* (2013.01); *A61B 5/6831* (2013.01)

(58) Field of Classification Search
CPC .............. A61B 5/6826; A61B 5/02438; A61B 5/14552; A61B 5/6831; A61B 5/02241; A61B 5/6838
See application file for complete search history.

(56) References Cited

U.S. PATENT DOCUMENTS

| | | | | |
|---|---|---|---|---|
| 5,209,230 A * | 5/1993 | Swedlow ............. | A61B 5/6838 356/41 |
| 5,438,986 A * | 8/1995 | Disch ................... | A61B 5/6826 600/479 |
| 2016/0143584 A1* | 5/2016 | Inagaki .............. | A61B 5/02416 600/300 |
| 2017/0014075 A1 | 1/2017 | Morimura et al. | |
| 2019/0298239 A1* | 10/2019 | Saeki ................... | A61B 5/6838 |
| 2022/0248984 A1* | 8/2022 | Poeze .................. | A61B 5/6816 |

FOREIGN PATENT DOCUMENTS

| | | |
|---|---|---|
| JP | 6554459 B2 | 7/2019 |
| JP | 7066485 B2 | 5/2022 |

* cited by examiner

*Primary Examiner* — Pascal M Bui Pho
*Assistant Examiner* — Lei Zhang
(74) *Attorney, Agent, or Firm* — Sughrue Mion, PLLC

(57) ABSTRACT

An assist tool to be attached to a finger of a subject. The assist tool includes a support body configured to be placed on a first side of the finger in a case where the support body is attached to the finger, a bag body configured to be placed on a second side of the finger, the second side being opposite to the first side with respect to the finger, a fluid passage communicating with inside of the bag body, and a size adjustment plate configured to be placed on one side, to which the finger is to be attached, in the support body. In a case where the size adjustment plate is accommodated in the support body, a finger accommodating space on a finger side of the bag body is thinned.

5 Claims, 11 Drawing Sheets

ASSIST TOOL AND SENSOR KIT

CROSS-REFERENCE TO RELATED APPLICATIONS

This application is based on and claims priority under 35 USC 119 from Japanese Patent Application No. 2023-191460 filed on Nov. 9, 2023, the entire content of which is incorporated herein by reference.

TECHNICAL FIELD

The presently disclosed subject matter relates to an assist tool to be attached to a finger of a subject and assist in obtaining physiological information on the subject by a sensor. The presently disclosed subject matter further relates to a sensor kit that obtains physiological information on a subject using the assist tool.

BACKGROUND ART

An example of obtaining physiological information includes measurement of capillary refill time. The capillary refill time is a simple indicator for assessing presence and absence of shock, and is a technique widely used in an emergency medical field such as determination of necessity of fluid and triage (priority evaluation in mass casualty situations). Specifically, a medical worker presses on a biological tissue such as a fingertip of a subject, and visually checks a color change in a nail and skin after releasing the pressure. If the color returns to normal within substantially two seconds, the subject is considered to be under a normal condition. Since this method involves manually pressing on the biological tissue and visually checking the color change of the skin, it lacks quantitativeness and is prone to measurement errors by an examiner.

Accordingly, JP6554459B specifies capillary refill time of a subject with a physiological information obtaining system using a sensor. In the physiological information obtaining system of JP6554459B, the sensor is attached to a finger of the subject by an assist tool, and physiological information is obtained from the sensor by changing pressure applied to the finger by a bag body of the assist tool. An assist tool of JP7066485B includes a support body and a bag body. A first side of a finger of a subject is placed on the support body. In this state, the bag body is placed on a second side of the finger by bending a hinge. At this time, a light emitter is placed on one of a pad side and a nail side, and a light detector is placed on the other side. Capillary refill time is specified from a change in a detected light intensity of the light detector when pressure by the bag body is released.

To perform a further reproducible and quantitative measurement of capillary refill time, pressure on a biological tissue needs to be constant. However, when a height or a width of a finger of a subject remarkably deviates from a size of an assist tool, the assist tool would not be attached with appropriate pressure for measuring the capillary refill time. For example, when the finger of the subject is excessively thin, a large gap is generated between a bag body and the finger, and pressure in measurement of the capillary refill time is not sufficient.

SUMMARY OF INVENTION

Aspects of certain non-limiting embodiments of the present disclosure address the features discussed above and/or other features not described above. However, aspects of the non-limiting embodiments are not required to address the above features, and aspects of the non-limiting embodiments of the present disclosure may not address features described above.

According to an aspect of the present disclosure, there is provided an assist tool to be attached to a finger of a subject, the assist tool assisting in obtaining physiological information on the subject, the assist tool including:

- a support body configured to be placed on a first side of the finger in a case where the support body is attached to the finger;
- a bag body configured to be placed on a second side of the finger, the second side being opposite to the first side with respect to the finger;
- a fluid passage communicating with inside of the bag body; and
- a size adjustment plate configured to be placed on a side of the support body, the finger being attached to the side of the support body,
- in which the first side is one of a pad side of the finger and a nail side of the finger,
- the second side is an other one of the pad side of the finger and the nail side of the finger,
- a sensor for obtaining the physiological information is configured to be placed between the finger and the support body, and between the finger and the bag body, and
- in a case where the size adjustment plate is accommodated in the support body, a finger accommodating space on a finger side of the bag body is thinned.

According to an aspect of the present disclosure, there is provided a sensor kit including:

- a sensor tool configured to obtain physiological information on a subject; and
- an assist tool configured to be attached to a finger of the subject to accommodate a sensor of the sensor tool and configured to assist in obtaining the physiological information on the subject by the sensor tool,
- in which the assist tool includes:
  - a support body configured to be placed on a first side of the finger;
  - a bag body configured to be placed on a second side of the finger, the second side being opposite to the first side of the finger;
  - a fluid passage communicating with inside of the bag body; and
  - a size adjustment plate configured to be placed on a side of the support body, the finger being attached to the side of the support body,
- the first side is one of a pad side of the finger and a nail side of the finger,
- the second side is an other one of the pad side of the finger and the nail side of the finger,
- a sensor for obtaining the physiological information is configured to be placed between the finger and the support body, and between the finger and the bag body, and
- in a case where the size adjustment plate is accommodated in the support body, a finger accommodating space on a finger side of the bag body is thinned.

BRIEF DESCRIPTION OF DRAWINGS

Exemplary embodiment(s) of the present invention will be described in detail based on the following figures, wherein.

DESCRIPTION OF EMBODIMENTS

Assist Tool of Comparative Example

Figure 1:
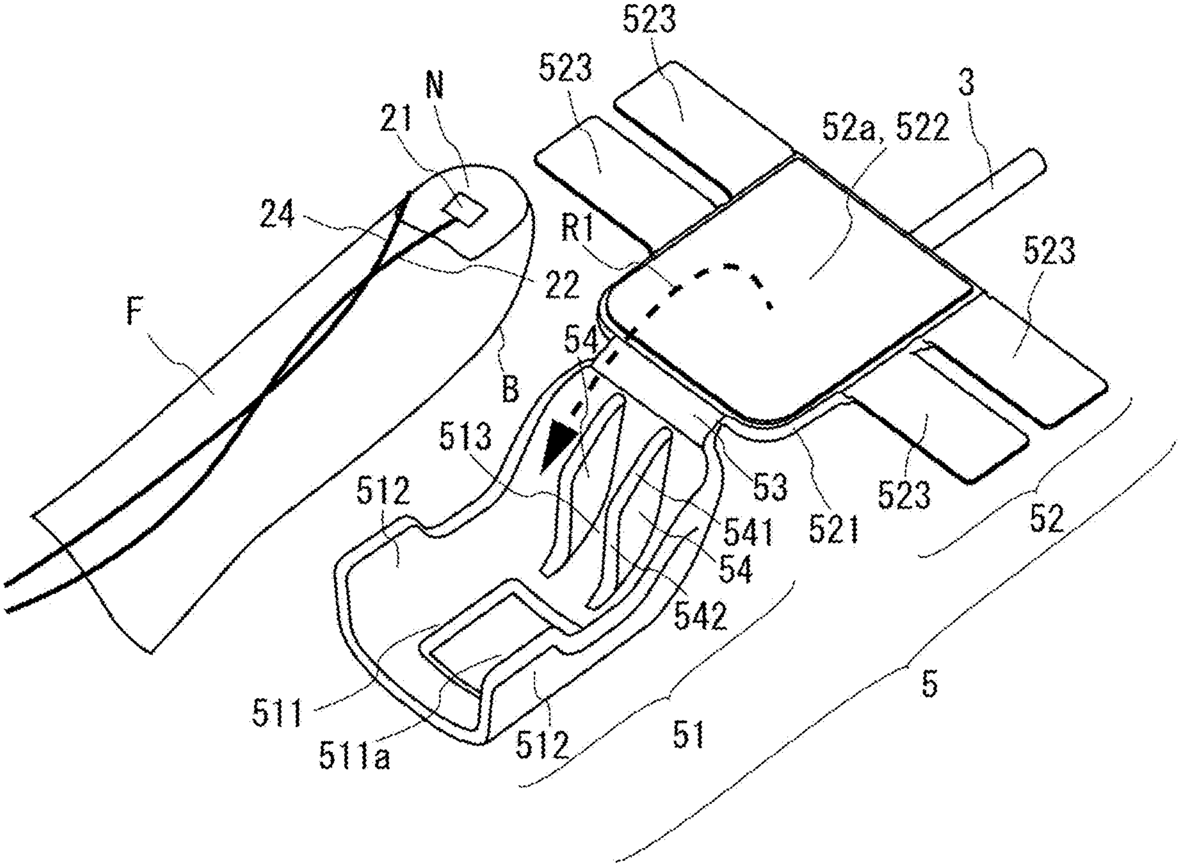
FIG. 1 is a perspective view illustrating a state immediately before a finger is inserted into an assist tool of a comparative example.

FIG. 1 is a perspective view illustrating a state immediately before a finger F is inserted into an assist tool 5 of a comparative example. A physiological information detector for obtaining physiological information on a subject is attached to the finger F. The physiological information detector of this example is a so-called pulse photometer probe, and includes a light emitter 21 and a light detector 23. In FIG. 1, the light emitter 21 is attached to a nail N, and the light detector 23 is hidden under the finger F. A sensor tool 2 can include the light emitter 21, a wire 22 connected to the light emitter 21, the light detector 23, and a wire 24 connected to the light detector 23. The light emitter 21 is an LED attached to the nail N. The light detector 23 hidden by the finger F is attached to a pad B side. The light emitter 21 is configured to emit light toward the light detector 23. The transmitted light is detected by the light detector 23 and a light detection signal is sent to the wire 24. The sensor tool 2 is attached by taping a tape (not illustrated) around the finger F.

The assist tool 5 is attached to the finger F of the subject, changes pressure to the finger F, and assists in obtaining the physiological information on the subject from the sensor tool 2. The assist tool 5 can include a support body 51, a lid body 52, and a hinge 53 connecting the support body 51 and the lid body 52. The assist tool 5 in FIG. 1 is in a state where the lid body 52 is open and the finger F is before being pressed in the support body 51. In the support body 51, side walls 512 rises from two sides of a bottom wall 511, and a rising portion 513 rises on a tip end side of the finger F. An upper end of the rising portion 513 is connected to the hinge 53.

The rising portion 513 is provided with two spacers 54. The spacers 54 have a plate shape, upper sides of the spacers 54 are inclining upper surfaces 541, and finger F sides of the spacers 54 are stopper surfaces 542. The inclining upper surfaces 541 gradually descend from the hinge 53 toward the nail N, and a sufficient gap G is provided between the inclining upper surfaces 541 and a bag film 522 of a bag body 52*a*. For this reason, in a case where the bag film 522 of the bag body 52*a* largely bulges downward, the bag film 522 can sufficiently press the nail N and the light emitter 21 without interfering with the spacers 54. Since the gap G due to the inclining upper surfaces 541 is defined, the finger F can be placed in an appropriate position of the assist tool 5 even for a subject having the long nail N.

The lid body 52 is provided with a lid body base 521, the bag film 522, and belts 523. Two of the belts 523 extend laterally from each of two sides of the lid body base 521. A part of the lid body base 521 and the bag film 522 form the bag body 52*a*. Inside of the bag body 52*a* communicates with inside of a tube 3. In the assist tool 5, in a case where the hinge 53 is bent and the lid body 52 is covered on the support body 51, the physiological information detector that is a sensor for obtaining physiological information is placed between the finger F and the support body 51 and between the finger F and the bag body 52*a*.

In FIG. 1, the finger F is accommodated between the side walls 512 in a state where the pad B side is placed on the bottom wall 511 via a tape. At this time, a tip end of the finger F abuts against the stopper surfaces 542. In a case where the lid body 52 is rotated as indicated by a dotted arrow R1, the hinge 53 is bent and the lid body 52 is covered on the finger F. A surface fastener (not illustrated) is provided on upper surfaces of the belts 523 and an outer surface of the support body 51 in FIG. 1. In a case where the belts 523 are wrapped around the outer surface of the support body 51 in a state where the lid body 52 is covered on the finger F, the lid body 52 can be fixed to the support body 51.

Figure 2:
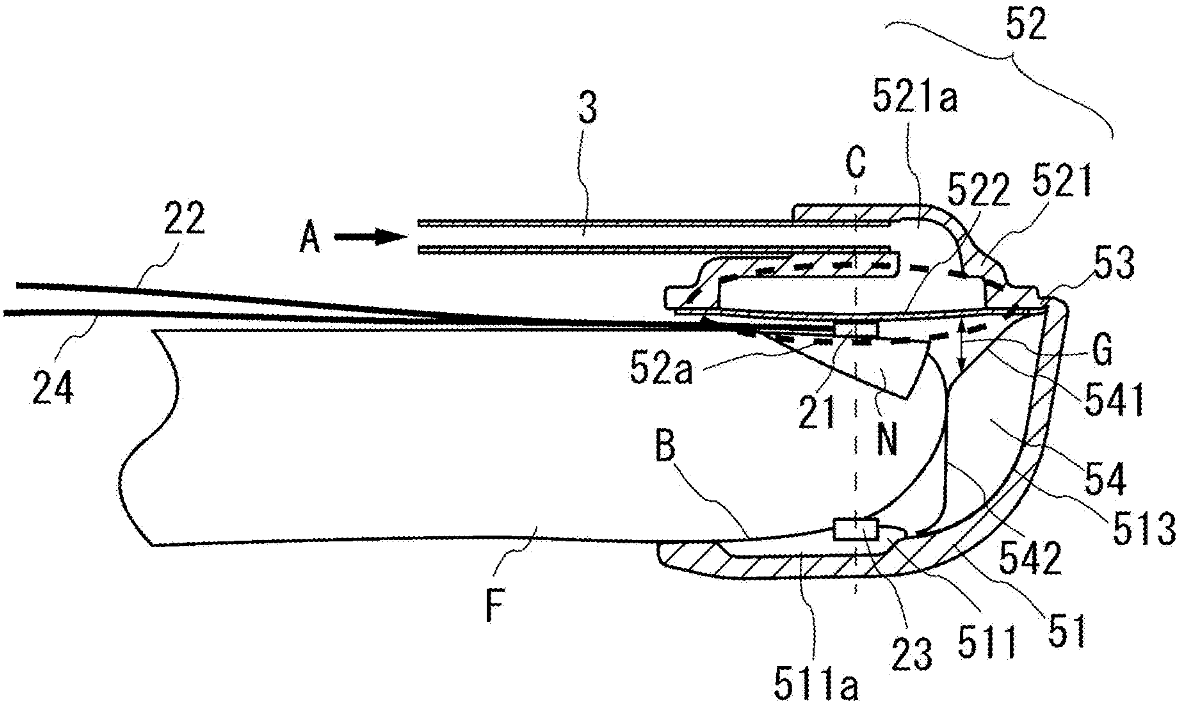
FIG. 2 is a sectional view illustrating a state where the finger is inserted into the assist tool of the comparative example and compressed air is supplied.

FIG. 2 is a sectional view of a state where the finger F is inserted into the assist tool 5 of the comparative example and the lid body 52 is closed. The assist tool 5 is illustrated in section, and the finger F and the sensor tool 2 such as the light emitter 21 are illustrated in side surfaces. The light emitter 21 is attached to the nail N of the finger F, and the light detector 23 is attached to the pad B side of the finger. Also in FIG. 2, a tape that taped peripheries of the finger F and the sensor tool 2 is not illustrated. Although not illustrated, in the state of FIG. 2, the belts 523 are wrapped around the outer surface of the support body 51, and the lid body 52 is fixed to the support body 51 by a surface fastener (not illustrated).

In FIG. 2, the hinge 53 is bent and the lid body 52 is covered on the finger F. In the lid body 52, the bag film 522 is bonded to a periphery of a lower surface of the lid body base 521, and forms the bag body 52*a* as illustrated by a dotted ellipse. A fluid passage 521*a* formed in an upper portion of the lid body base 521 communicates with the inside of the bag body 52*a*, and an opposite side is connected to the tube 3. The pad B of the finger F located under the bag body 52*a* is in contact with the bottom wall 511 of the support body 51. The light detector 23 is fitted into a concave portion 511*a* provided in the bottom wall 511. Since the concave portion 511*a* is provided in the bottom wall 511, the finger F is pressed from above and the pad B is fitted into the concave portion 511*a* and is less likely to be removed from the assist tool 5.

In FIG. 2, the support body 51 of the assist tool 5 is provided with the spacers 54 such that the finger F does not enter a hinge 53 side on a fingertip side of the bag body 52*a*, and the tip end of the finger F reaches the stopper surfaces 542 of the spacers 54. The light emitter 21 and the light detector 23 are provided substantially in a position of a center line of the nail N. In FIG. 2, a bag body center line C passes through the light emitter 21 and the light detector 23. Since the tip end of the finger F is pressed by the stopper surfaces 542 of the spacers 54, a center of the nail N substantially passes through the bag body center line C.

As described above, presence of the spacers 54 facilitates alignment of center positions of the nail N and the bag body 52*a*. Accordingly, efficient pressing and stable capillary refill time measurement can be implemented. The number of the spacers 54 may be one, and when there are two spacers as in an embodiment, the spacers 54 abut against the tip end of the finger F in two positions when being attached to the finger F with improved stability and attachment comfort.

As indicated by an arrow A, compressed air is supplied from the tube 3 to the bag body 52*a* in FIG. 2, and the bag film 522 bulges downward. The bag body center line C, which is a center line of the bag body 52*a*, passes through the nail N. In this state, pressing by the bag body 52*a* sufficiently acts on the nail N to discharge blood of a capillary. For this reason, capillary refill time can be measured favorably.

Figure 3:
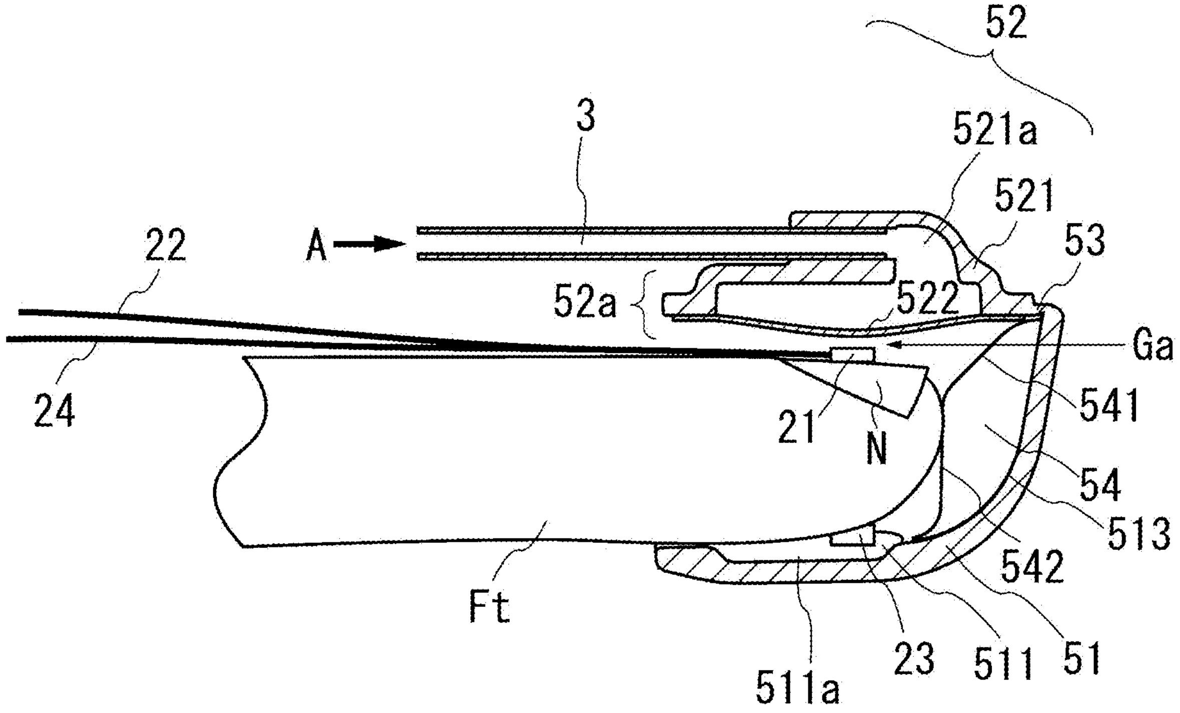
FIG. 3 is a sectional view illustrating a state where a thin finger is inserted into the assist tool of the comparative example and a lid body is closed.

However, as illustrated in FIG. 2, the finger F may not have a thickness suitable for the assist tool 5. FIG. 3 illustrates a sectional view when the assist tool 5 is used for a thin finger Ft. Similar to or the same as FIG. 2, the assist tool 5 is illustrated in section, and the thin finger Ft and the sensor tool 2 such as the light emitter 21 are illustrated in side surfaces.

Also in FIG. 3, compressed air is supplied from the tube 3 to the bag body 52*a* as indicated by the arrow A, and the bag film 522 bulges downward. However, a gap Ga is generated between the bag film 522 of the bag body 52*a* and the light emitter 21 since the finger Ft is thin. For this reason, pressure is not transmitted to the thin finger Ft or the nail N, appropriate pressing is not performed, and the capillary refill time cannot be measured.

Example 1

Figure 4:
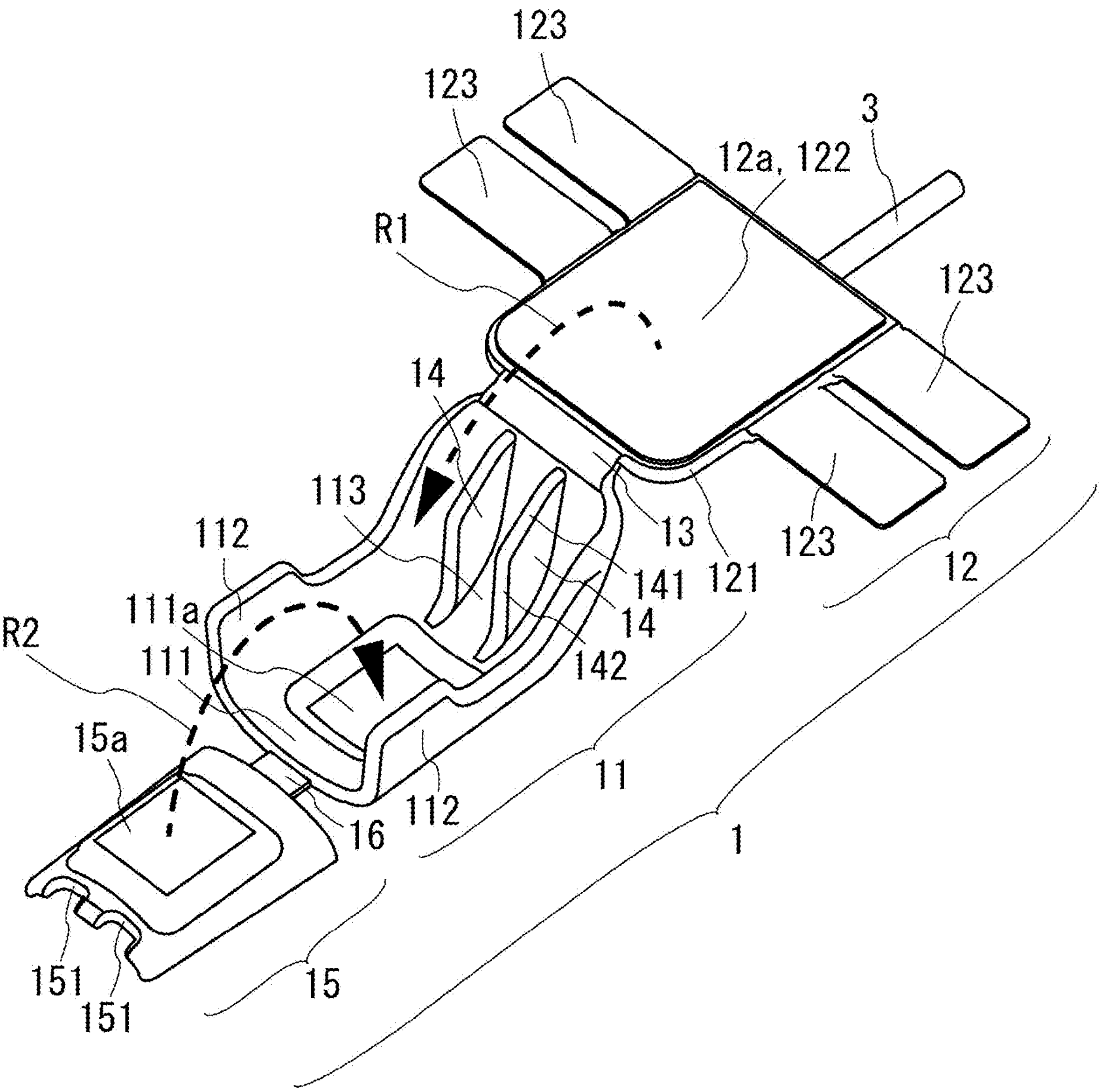
FIG. 4 is a perspective view of an assist tool according to an embodiment of the presently disclosed subject matter.

FIG. 4 is a perspective view of an assist tool 1 according to Example 1 of the presently disclosed subject matter. Similar to or the same as the assist tool 5 in the comparative example in FIGS. 1 and 2, the assist tool 1 is attached to the finger F of a subject to whom the sensor tool 2 is attached, and assists in obtaining physiological information on the subject from the sensor tool 2. The assist tool 1 can include a support body 11, a lid body 12, and a hinge 13 connecting the support body 11 and the lid body 12. The assist tool 1 in FIG. 4 is in a state in which the lid body 12 is open, and the finger F is before being placed in the support body 11. In the support body 11, side walls 112 rises from two sides of a bottom wall 111, and a rising portion 113 rises on a tip end side of a position in which the finger F is inserted to face a fingertip. The rising portion 113 is provided with two spacers 14. The spacers 14 have a plate shape, upper sides of the spacers are inclining upper surfaces 141, and finger F sides are stopper surfaces 142. The sensor tool 2 and the assist tool 1 are combined and sold and distributed as a sensor kit.

The lid body 12 of FIG. 4 is provided with a lid body base 121, a bag film 122, and belts 123. Two of the belts 123 extend laterally from each of two sides of the lid body base 121. A part of the lid body base 121 and the bag film 122 constitute a bag body 12*a*. Inside of the bag body 12*a* communicates with inside of the tube 3. In the assist tool 1, a sensor physiological information detector for obtaining physiological information is placed between the finger F and the support body 11 and between the finger F and the bag body 12*a*.

Also in the assist tool 1 of FIG. 4, the finger F is accommodated between the side walls 112 in a state where the pad B side is placed on the bottom wall 111 via a tape. In a case where the lid body 12 is rotated as indicated by the dotted arrow R1, the hinge 13 is bent and the lid body 12 is covered on the finger F. A surface fastener (not illustrated) is provided on upper surfaces of the belts 123 and an outer surface of the support body 11 in FIG. 4. In a case where the belts 123 are wrapped around the outer surface of the support body 11 in a state where the lid body 12 is covered on the finger F, the lid body 12 can be fixed to the support body 51. Accordingly, the light detector 23 is placed between the finger F and the support body 11, and the light emitter 21 is placed between the finger F and the bag body 12*a* as a physiological information detector for obtaining physiological information.

Figure 5:
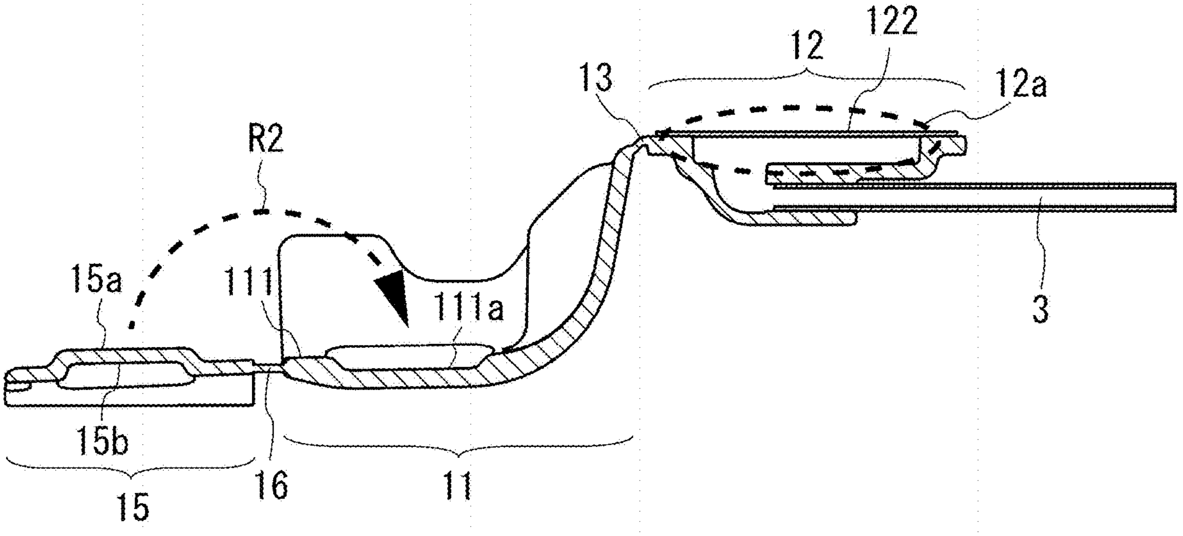
FIG. 5 is a sectional view of an assist tool of Example 1 in an open state.
Figure 6:
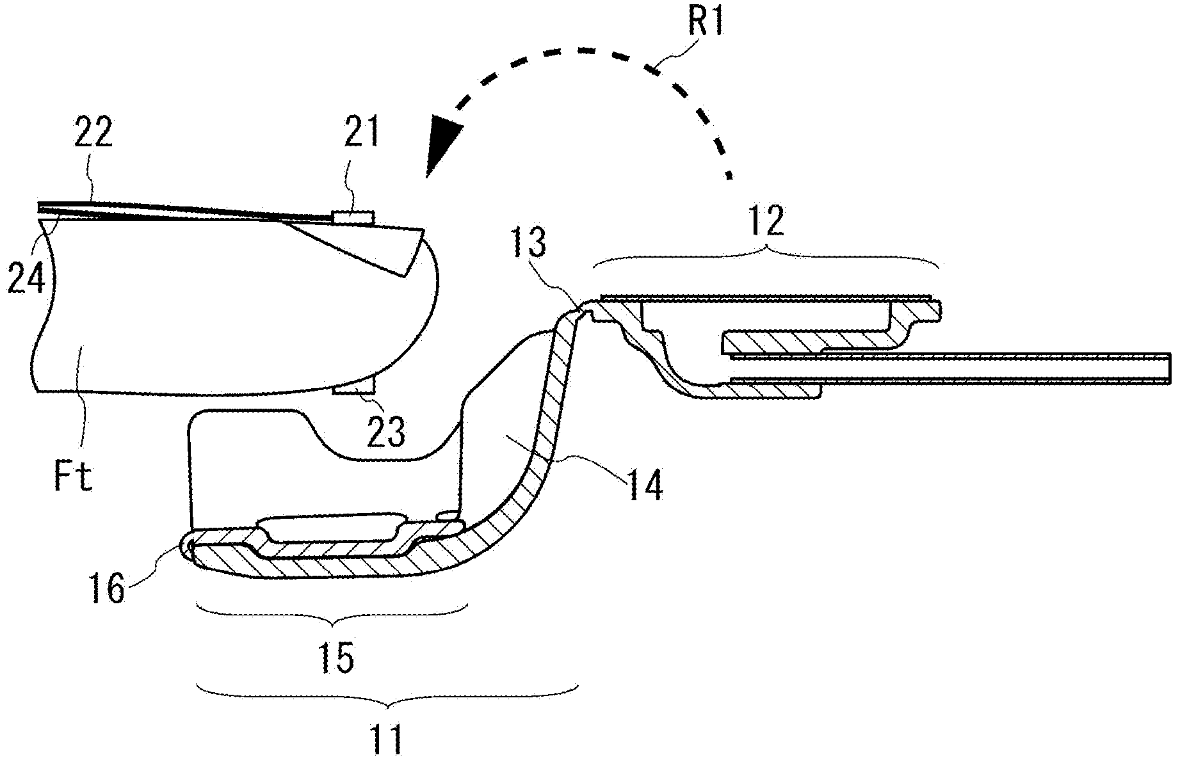
FIG. 6 is a sectional view of the assist tool of Example 1 in which a size adjustment plate is accommodated in a support body.

The assist tool 1 of Example 1 is similar to or the same as the assist tool 5 of the comparative example in the above aspects, and is further provided with a size adjustment plate 15 as illustrated in FIG. 4. The size adjustment plate 15 is connected to a position opposite to the hinge 13 in the support body 11 via a connection portion 16. The connection portion 16 has a small width, is thinner than the support body 11 and the size adjustment plate 15, and configured to bend due to flexibility thereof. FIGS. 5 and 6 are sectional views of the assist tool 1 of Example 1. FIG. 5 is a sectional view of the assist tool 5 before the connection portion 16 is bent, and FIG. 6 is a sectional view of the assist tool 5 after the connection portion 16 is bent.

In FIG. 5, similar to or the same as FIG. 4, the connection portion 16 of the assist tool 1 is not bent, and extends linearly from the size adjustment plate 15 and is connected to the support body 11. The hinge 13 is not bent, and the bag film 122 of the bag body 12*a* faces upward. In this state, the size adjustment plate 15 is formed with a convex portion 15*a* on an upper surface of the size adjustment plate 15 and a concave portion 15*b* in a lower surface of the size adjustment plate 15. A concave portion 111*a* is provided in the bottom wall 111 of the support body 11. In a case where the assist tool 1 is used for the thin finger Ft, the size adjustment plate 15 is rotated in a direction of a dotted arrow R2 to bend the connection portion 16, and the convex portion 15*a* of the size adjustment plate 15 is fitted into the concave portion 111*a* of the bottom wall 111.

FIG. 6 illustrates a state where the convex portion 15*a* of the size adjustment plate 15 is fitted into the concave portion 111*a*. FIG. 6 illustrates a section of the assist tool 1 in which the size adjustment plate 15 is superimposed on the support body 11, and a side surface of the thin finger Ft to which the light emitter 21 and the like is attached. The size adjustment plate 15 is accommodated in the support body 11, and recesses and protrusions of the size adjustment plate 15 is interlocked with those of the support body 11. FIG. 6 illustrates a state immediately before the thin finger Ft is placed in the support body 11. Also in this drawing, a tape wound around the thin finger Ft is omitted. Although hidden in FIG. 6, the size adjustment plate 15 avoids lower portions of the spacers 14 by spacer avoidance 151 illustrated in FIG. 4.

Figure 7:
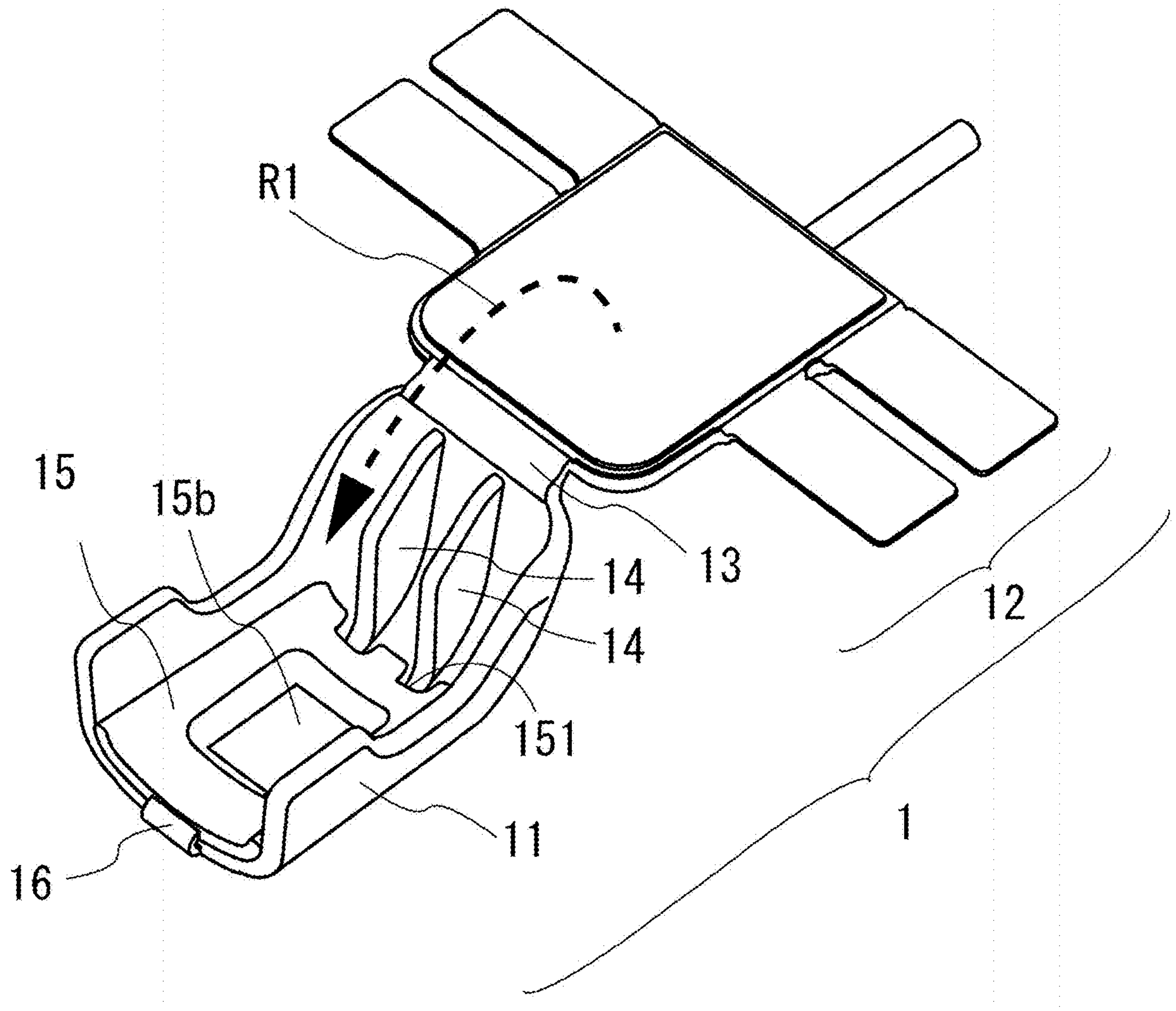
FIG. 7 is a perspective view of the assist tool of Example 1 in which the size adjustment plate is accommodated in the support body.

FIG. 7 illustrates the assist tool 1 in the state of FIG. 6 as viewed obliquely from above. The connection portion 16 is bent, and the size adjustment plate 15 enters the support body 11. Inside of the support body 11 is raised by the size adjustment plate 15. The size adjustment plate 15 avoids the lower portions of the spacers 14 by the spacer avoidance 151.

In FIGS. 6 and 7, after the thin finger Ft is placed on the size adjustment plate 15, the lid body 12 is rotated in the direction of the dotted arrow R1 and covered on the thin finger Ft. Then, the belts 123 are wrapped around the outer surface of the support body 11 in a state where the lid body 12 is covered on the thin finger Ft, so that the lid body 12 is fixed to the support body 11. In FIGS. 6 and 7, the size adjustment plate 15 is in contact with a bottom portion of the support body 11. However, even in a non-contact state, the thin finger Ft is placed on the size adjustment plate 15 and is pressed from above, the connection portion 16 is sufficiently bent, and the size adjustment plate 15 is folded and accommodated in a lower portion of the support body 11.

Figure 8:
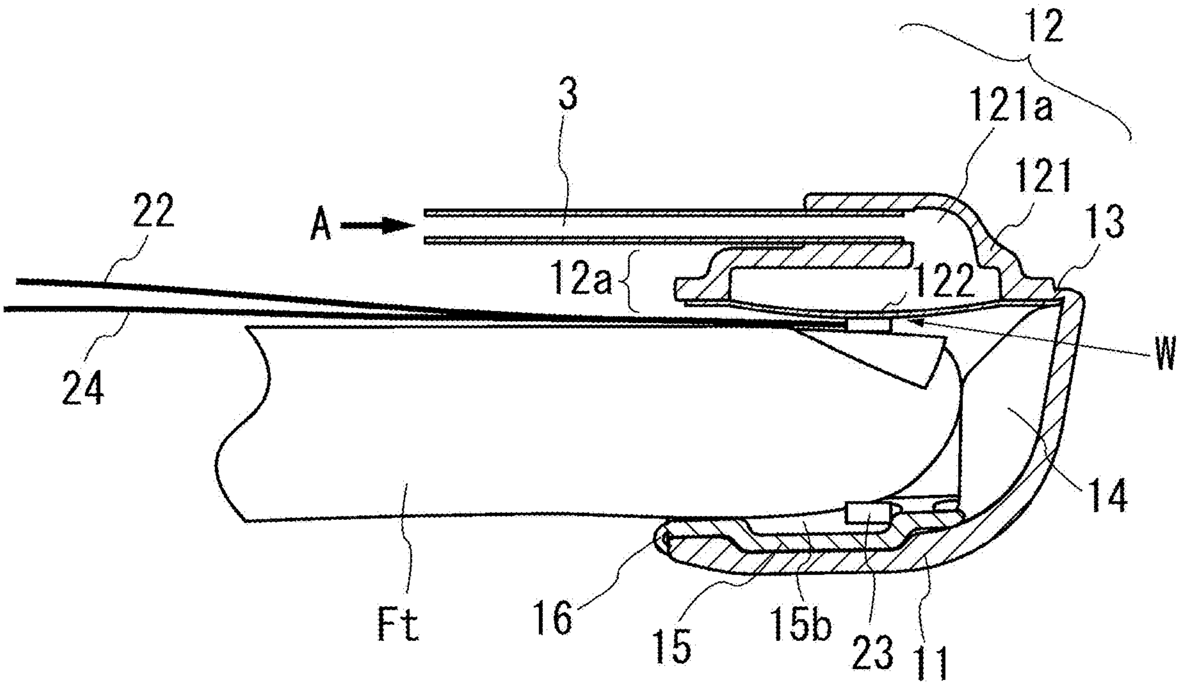
FIG. 8 is a sectional view illustrating a state in which a thin finger is inserted into the assist tool of Example 1 and a lid body is closed.

FIG. 8 illustrates a sectional view when the assist tool 1 with the size adjustment plate 15 folded is used for the thin finger Ft. Similar to or the same as FIGS. 2 and 3, the assist tool 1 is illustrated in section, and the thin finger Ft and the sensor tool 2 such as the light emitter 21 are illustrated in side surfaces. The physiological information detector, which is a sensor, can include the light emitter 21 and the light detector 23. Also in FIG. 8, compressed air is supplied from the tube 3 to the bag body 12*a* as indicated by the arrow A, and the bag film 122 bulges downward. The light detector 23 is accommodated in the concave portion 15*b* of the size adjustment plate 15. In a case where the size adjustment plate 15 is accommodated in the support body 11, in the assist tool 1 in which the lid body 12 is closed, a finger accommodating space defined on a support body 11 side of the bag film 122 of the bag body 12*a* is thinned.

Figure 9:
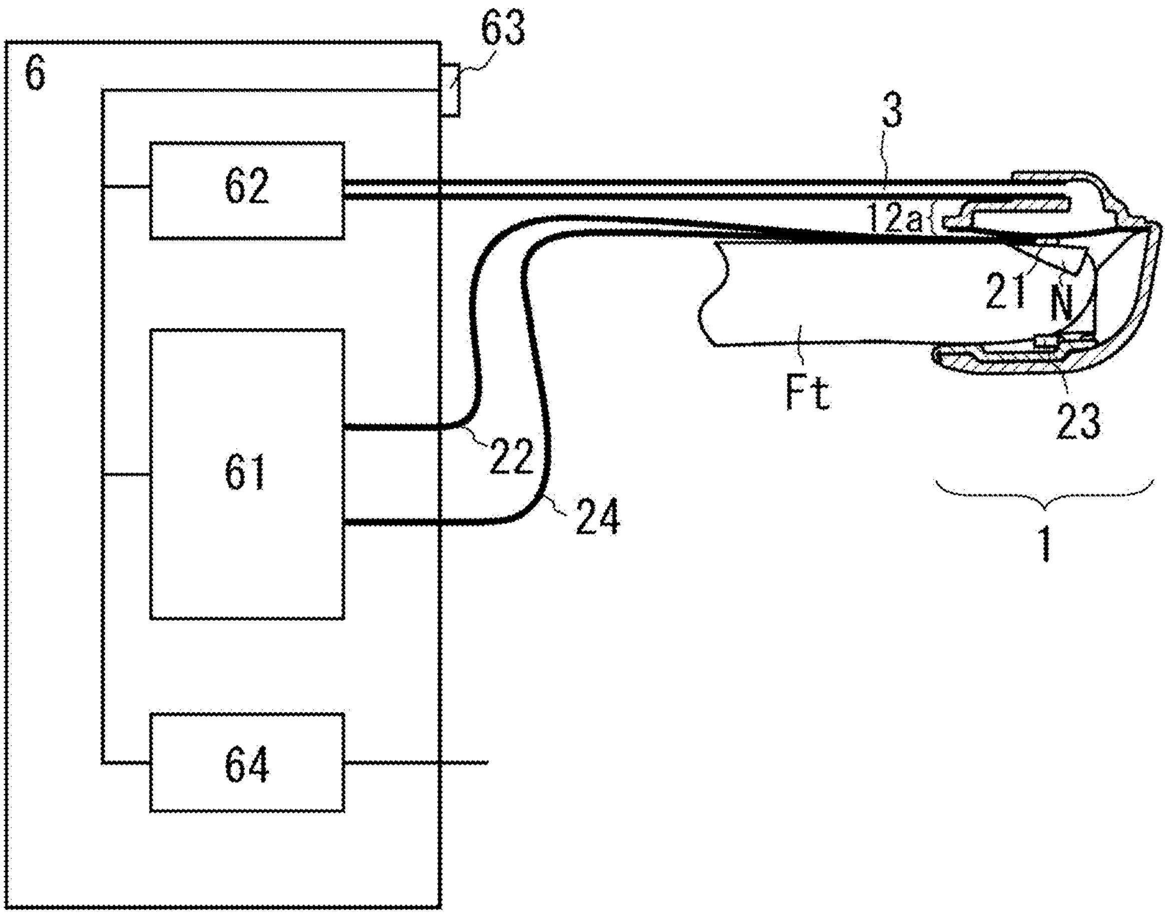
FIG. 9 illustrates a situation of obtaining physiological information using the assist tool of Example 1.

In a state in which the sensor tool 2 and the assist tool 1 are attached to the thin finger Ft as illustrated in FIG. 8, physiological information is obtained by a physiological information obtaining device 6. FIG. 9 illustrates a situation of obtaining physiological information using the assist tool 1 of an embodiment. The assist tool 1, the light emitter 21, the wire 22, the light detector 23, the sensor tool 2 with the wire 24, and the tube 3 are illustrated in FIG. 6. The tube 3 and the wires 22 and 24 are connected to the physiological information obtaining device 6. The physiological information obtaining device 6 can include an information obtaining unit 61, a pressure adjustment unit 62, a switch 63, and an information output unit 64. The information obtaining unit 61, the pressure adjustment unit 62, the switch 63, and the information output unit 64 are connected to each other inside the physiological information obtaining device 6.

The wires 22 and 24 are connected to the information obtaining unit 61, and the light emitter 21 emits light and a detected light amount of the light detector 23 is obtained. This makes it possible to calculate capillary refill time. Since the sensor tool 2 functions as a probe of a pulse oximeter, the information obtaining unit 61 can obtain other physiological information such as non-invasive arterial blood oxygen saturation (SpO2).

The tube 3 is connected to the pressure adjustment unit 62, and compressed air is supplied into and removed from the tube 3 by opening an air valve (not illustrated). The switch 63 is used to start obtaining the physiological information, and the information output unit 64 outputs the physiological information obtained by the physiological information obtaining device 6 to outside as information data, display information, and audio information.

In FIG. 9, in a case where the switch 63 is pressed and turned ON, compressed air is supplied from the pressure adjustment unit 62 to the tube 3. The supplied compressed air inflates the bag body 12*a* of the assist tool 1 and presses the nail N of the thin finger Ft. Accordingly, blood is pushed out from a capillary in a vicinity of the nail N. Light transmitted from the light emitter 21 is detected by the light detector 23 without much absorption of light by the blood.

When prescribed time elapses, the pressure adjustment unit 62 stops supplying compressed air and removes the compressed air to reduce the pressure. At this time, the nail N is released from being pressed by the bag body 12*a* of the assist tool 1. Then, the blood returns to or does not return to the capillary in the vicinity of the nail N depending on a state of the subject. Light transmitted from the light emitter 21 is detected by the light detector 23 with a changed light absorption depending on a degree of return of the blood. The information obtaining unit 61 measures the capillary refill time based on a change in the detected light amount after the pressure adjustment unit 62 reduces the pressure. The information obtaining unit 61 can further obtain other physiological information such as non-invasive arterial blood oxygen saturation (SpO2) when no pressure is generated by the pressure adjustment unit 62.

The capillary refill time and other physiological information measured by the information obtaining unit 61 are output from the information output unit 64. This output can be performed in a form of information data, display information, audio information, and the like.

As illustrated in FIG. 8, in a case of the thin finger Ft, the assist tool 1 with the thinned finger accommodating space can be used by folding the size adjustment plate 15 and raising the assist tool 1. For this reason, no gap Ga is generated between the bag film 122 of the bag body 12*a* and the light emitter 21 indicated by an arrow W. Pressure is transmitted from the bag body 12*a* to the thin finger Ft and the nail N thereof, appropriate pressing is performed, and the capillary refill time can be measured.

Figure 10:
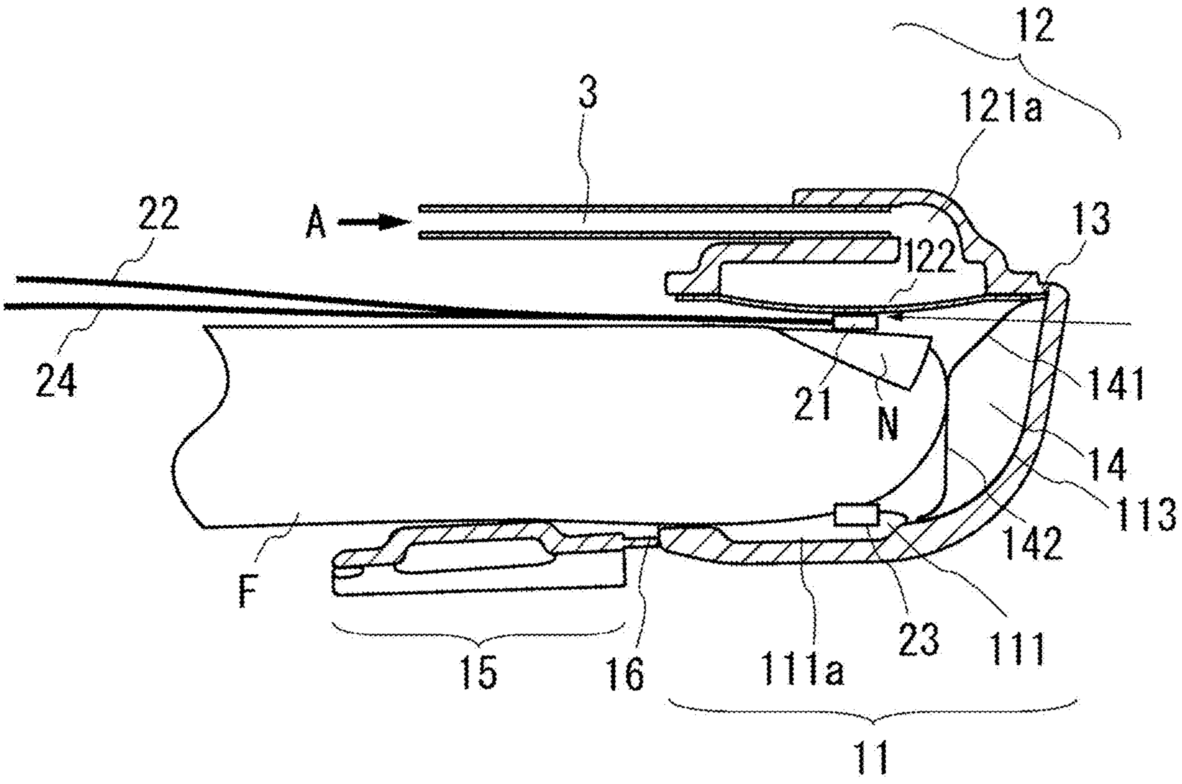
FIG. 10 is a sectional view illustrating a state in which a finger is inserted into the assist tool of Example 1 and the lid body is closed.

On the other hand, the assist tool 1 can also be used for the finger F of a normal thickness. FIG. 10 is a sectional view illustrating a state in which the finger F is inserted into the assist tool 1 of Example 1 and the lid body 12 is closed. In a case where the assist tool 1 is used for the finger F having a normal thickness, the connection portion 16 is not bent, and the size adjustment plate 15 is not accommodated in the support body 11. As a result, an appropriate space for the finger F is ensured inside the assist tool 1 in which the lid body 12 is closed without raising by the size adjustment plate 15.

When used for the finger F having a normal thickness, the connection portion 16 may be used in an extending state as illustrated in FIG. 10. Alternatively, the size adjustment plate 15 may be connected to the support body 11 via the cuttable connection portion 16, and may also be cut off at the connection portion 16 and removed from the support body 11. When used for the thin finger Ft, the size adjustment plate 15 that is cut off at the connection portion 16 and separated from the support body 11 may be accommodated in the support body 11 and used. The size adjustment plate 15 can be attached to a side of the support body 11 to which the finger is attached, regardless of whether being connected by the connection portion 16, and the finger accommodating space can be thinned by attaching the size adjustment plate 15.

Example 2

Figure 11:
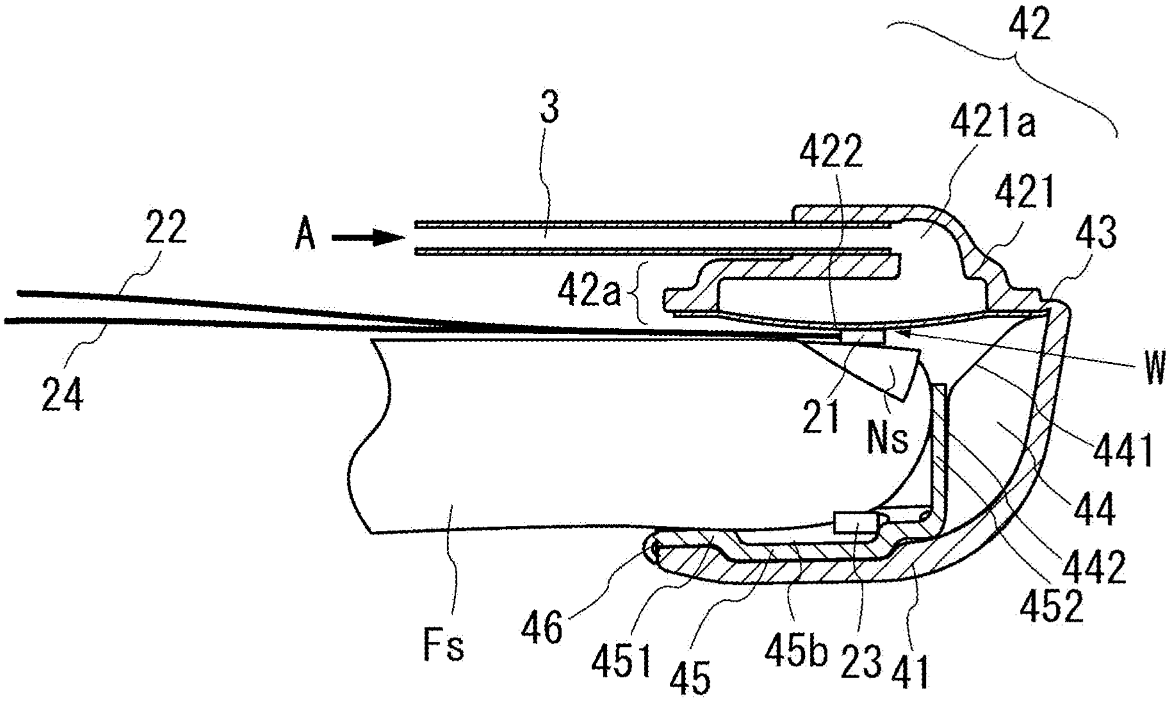
FIG. 11 is a sectional view illustrating a state in which a small finger is inserted into an assist tool of Example 2 and a lid body is closed.

FIG. 11 illustrates a sectional view of an assist tool 4 according to Example 2 of the presently disclosed subject matter. The assist tool 4 is attached to a small finger Fs of a subject to whom the sensor tool 2 is attached, and assists in obtaining physiological information on the subject from the sensor tool 2. The assist tool 4 can include a support body 41, a lid body 42, and a hinge 43 connecting the support body 41 and the lid body 42. The assist tool 4 in FIG. 11 is in a state in which the lid body 42 is closed and the small finger Fs is placed in the support body 41.

FIG. 11 illustrates a sectional view when the assist tool 4 with a size adjustment plate 45 folded is used for the small finger Fs. Similar to or the same as FIGS. 2, 3, 8, and 10, the assist tool 4 is illustrated in section, and the small finger Fs and the sensor tool 2 such as the light emitter 21 are illustrated in side surfaces. The physiological information detector, which is a sensor, can include the light emitter 21 and the light detector 23. In FIG. 11, the support body 41 of the assist tool 4 is provided with a spacer 44 on a hinge 43 side on a fingertip side of a bag body **42*a*. The spacer 44 can include an inclining upper surface 441 and a stopper surface 442 as in Example 1. Also in FIG. 11, compressed air is supplied from the tube 3 to the bag body 42*a* as indicated by the arrow A, and a bag film 422 bulges downward. The light detector 23 is accommodated in a concave portion 45*b* formed in a finger thickness adjustment portion 451 of the size adjustment plate 45**.

Different from the assist tool 1 of Example 1 illustrated in FIGS. 4 to 10, the assist tool 4 of Example 2 illustrated in FIG. 11 can include a fingertip adjustment portion 452. In the size adjustment plate 45 of the assist tool 4, the finger thickness adjustment portion 451 is connected to the support body 41 by a connection portion 46. In the size adjustment plate 45, a side of the finger thickness adjustment portion 451 that is opposite to the connection portion 46 is bent to form the fingertip adjustment portion 452. Other configurations are the same as those of the assist tool 1 of Example 1.

As illustrated in FIG. 11, in a case of the small finger Fs, the finger is raised by the finger thickness adjustment portion 451 when the size adjustment plate 45 of the assist tool 4 is folded, and the fingertip adjustment portion 452 further abuts against the stopper surface 442 of the spacer 44. A position of a fingertip can be deviated rearward from the stopper surface 442 by the fingertip adjustment portion 452. A finger accommodating space is thinned by the raising of the finger thickness adjustment portion 451, no gap Ga is generated between the bag film 422 of the bag body **42*a* and the light emitter 21 indicated by the arrow W. Pressure is transmitted from the bag body 42*a*** to the small finger Fs and a small nail Ns, appropriate pressing is performed, and the capillary refill time can be measured.

In the size adjustment plate 45 of Example 2, a plate of the finger thickness adjustment portion 451 and a plate of the fingertip adjustment portion 452 are formed substantially at a right angle. Alternatively, the size adjustment plate 45 may be formed of a flexible member such as silicon rubber, and may be bent when the small finger Fs is pressed against the size adjustment plate 45 to serve as the finger thickness adjustment portion 451 and the fingertip adjustment portion 452.

Example 1 illustrates the assist tool 1 corresponding to the normal finger F and the thin finger Ft, and Example 2 illustrates the assist tool 4 corresponding to the normal finger F and the small finger Fs. However, when a subject has a thick finger, the fixed finger is pressed against a corner, which inhibits blood re-inflow in measurement of the capillary refill time. Further, for a large finger, the bag body center line C may deviate from a nail center. When the assist tools 1 and 4 in Examples 1 and 2 are larger, the assist tools 1 and 4 can be used as assist tools corresponding to subjects having a thick finger, a large finger and the normal finger F. When the assist tools 1 and 4 are slightly larger, the assist tools 1 and 4 can be used as assist tools corresponding to a range from the normal finger F to a slightly thick finger or a slightly thin finger.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

In the assist tools 1 and 4 of Examples 1 and 2, the support bodies 11 and 41 are placed on a pad side of the finger F, the thin finger Ft, and the small finger Fs, and the bag bodies **12*a* and 42*a*** are placed on a nail side. Alternatively, this may be reversed. In summary, a first side is one of the pad side and the nail side, and a second side is the other one of the pad side and the nail side. The support body is placed on the first side of the finger, and the bag body is placed on the second side of the finger opposite to the first side.

What is claimed is:

1. An assist tool to be attached to a finger of a subject, the assist tool assisting in obtaining physiological information on the subject, the assist tool comprising:
- a support body configured to be placed on a first side of the finger in a case where the support body is attached to the finger;
- a bag body configured to be placed on a second side of the finger, the second side being opposite to the first side with respect to the finger;
- a fluid passage communicating with inside of the bag body; and
- a size adjustment plate configured to be placed on one side of the support body to which the finger is to be attached,
- wherein the first side is one of a pad side of the finger and a nail side of the finger,
- the second side is an other one of the pad side of the finger and the nail side of the finger,
- a sensor for obtaining the physiological information includes a first sensor part configured to be placed between the finger and the support body, and a second sensor part configured to be placed between the finger and the bag body,
- in a case where the size adjustment plate is accommodated in the support body, a finger accommodating space on a finger side of the bag body is thinned, and the first sensor part is configured to be placed between the finger and the size adjustment plate, and
- the bag body is connected to the support body by a hinge provided at a first end of the support body, and the size adjustment plate is connected to the support body by a connection portion provided at a second end of the support body opposite to the hinge.

2. The assist tool according to claim 1,
- wherein the size adjustment plate is connected to the support body by the connection portion configured to be cut off.

3. The assist tool according to claim 1, wherein the size adjustment plate is connected to the support body by the connection portion configured to be bent, and the size adjustment plate is accommodated in the support body by bending the connection portion.

4. The assist tool according to claim 1, wherein in a case where the size adjustment plate is accommodated in the support body, a recess and a protrusion of the size adjustment plate is interlocked with the support body.

5. A sensor kit comprising:

a sensor tool configured to obtain physiological information on a subject; and an assist tool configured to be attached to a finger of the subject to accommodate a sensor of the sensor tool and configured to assist in obtaining the physiological information on the subject by the sensor tool, wherein the assist tool includes:

a support body configured to be placed on a first side of the finger;

a bag body configured to be placed on a second side of the finger, the second side being opposite to the first side of the finger;

a fluid passage communicating with inside of the bag body; and a size adjustment plate configured to be placed on one side of the support body to which the finger is to be attached, the first side is one of a pad side of the finger and a nail side of the finger, the second side is an other one of the pad side of the finger and the nail side of the finger, a sensor for obtaining the physiological information comprises a first sensor part configured to be placed between the finger and the support body, and a second sensor part configured to be placed between the finger and the bag body, and in a case where the size adjustment plate is accommodated in the support body, a finger accommodating space on a finger side of the bag body is thinned, and the first sensor part is configured to be placed between the finger and the size adjustment plate, and the bag body is connected to the support body by a hinge provided at a first end of the support body, and the size adjustment plate is connected to the support body by a connection portion provided at a second end of the support body opposite to the hinge.

* * * * *